United States Patent [19]

Schönafinger et al.

[11] 4,416,893
[45] Nov. 22, 1983

[54] SUBSTITUTED 1,2,5-OXADIAZOLE-2-OXIDES IN HUMAN CARDIOVASCULAR SYSTEM DISEASE

[75] Inventors: Karl Schönafinger; Rudi Beyerle; Anton Mogilev, all of Frankfurt am Main; Helmut Bohn, Schöneck; Piero Martorana, Bad Homburg; Rolf-Eberhard Nitz, Frankfurt am Main, all of Fed. Rep. of Germany

[73] Assignee: Cassella Aktiengesellschaft, Frankfurt am Main, Fed. Rep. of Germany

[21] Appl. No.: 246,954

[22] Filed: Mar. 24, 1981

[30] Foreign Application Priority Data

Apr. 2, 1980 [DE] Fed. Rep. of Germany ....... 3012862

[51] Int. Cl.³ .............................................. A61K 31/42
[52] U.S. Cl. .................................... 424/272; 548/125
[58] Field of Search ........................................ 424/272

[56] References Cited

PUBLICATIONS

*Chemical Abstracts,* 83:90988u and 108147f, (1975), [Fundaro, A., *Boll. Soc. Ital. Biol. Sper.,* 1974, 50(20), 1650-1653 and 1654-1657].
Gasco, A., et al., *J. Het. Chem.,* 9, 837-841 and 577-580, (1972).
Wieland, H., et al., *Liebigs Ann. Chem.,* 367, 80 (1909).
Grundmann, C., et al., *Liebigs Ann. Chem.,* 1975, 1029.
Ponzio, G., *Gazz. Chim. Ital.,* 66, 819 (1936).
Fundaro, A., *Boll. Soc. Ital. Biol. Sper.,* 1974, 50(20), 1650-1657.
Dimroth, O., et al., *Ber.* 41, 4068-4083, (1908).

*Primary Examiner*—Richard A. Schwartz
*Attorney, Agent, or Firm*—Berman, Aisenberg & Platt

[57] ABSTRACT

Pharmaceutical compositions comprising as pharmacologically active component a 1,2,5-oxadiazole-2-oxide of the general formula I

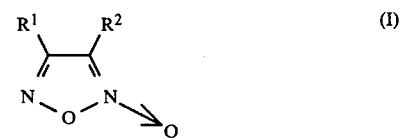

wherein $R^1$ and $R^2$ have the following meaning:

| $R^1$ | $R^2$ |
|---|---|
| 1. $CO-NH_2$ | $CH_3$ |
| 2. $COOC_2H_5$ | $CH_3$ |
| 3. $CO-NHNH_2$ | $CH_3$ |
| 4. $COOH$ | $CH_3$ |
| 5. $-NH-COOC_2H_5$ | $CH_3$ |
| 6. $-NH-COOC_3H_7(n)$ | $CH_3$ |
| 7. $-NH-COOC_3H_7(i)$ | $CH_3$ |
| 8. $-NH-COOC_4H_9(n)$ | $CH_3$ |
| 9. $-NH-COOCH_2-phenyl$ | $CH_3$ |
| 10. $CO-NH_2$ | $CO-NH_2$ |
| 11. $CN$ | $CN$ |
| 12. $COOH$ | $COOCH_3$ |
| 13. $COOCH_3$ | $COOCH_3$ |
| 14. $COOC_2H_5$ | $COOC_2H_5$ |
| 15. $CH_3$ | $CO-NH_2$ |
| 16. $CH_3$ | $COOC_2H_5$ |
| 17. $CH_3$ | $CO-NHNH_2$ |
| 18. $CH_3$ | $COOH$ |
| 19. $CN$ | $CO-NH_2$ |
| 20. $CO-NH-phenyl$ | $CO-NH-phenyl$ |
| 21. $CH_3$ | $NH-COOC_2H_5$ |
| 22. $CH_3$ | $NH-COOC_3H_7(n)$ |
| 23. $CH_3$ | $NH-COOC_3H_7(i)$ |
| 24. $CH_3$ | $NH-COOC_4H_9(n)$ |
| 25. $CH_3$ | $NH-COOCH_2-phenyl$ |
| 26. $CO-NH-phenyl$ $CH_3$ | $CH_3$ or $CO-NH-phenyl$ |

They are useful for treating or preventing cardiovascular system disease in man.

9 Claims, No Drawings

SUBSTITUTED 1,2,5-OXADIAZOLE-2-OXIDES IN HUMAN CARDIOVASCULAR SYSTEM DISEASE

The present invention relates to 1,2,5-oxadiazole-2-oxides of the general formula I

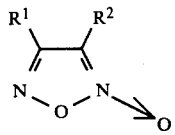

wherein $R^1$ and $R^2$ have the following meaning:

| | $R^1$ | $R^2$ |
|---|---|---|
| 1. | CO—NH$_2$ | CH$_3$ |
| 2. | COOC$_2$H$_5$ | CH$_3$ |
| 3. | CO—NHNH$_2$ | CH$_3$ |
| 4. | COOH | CH$_3$ |
| 5. | —NH—COOC$_2$H$_5$ | CH$_3$ |
| 6. | —NH—COOC$_3$H$_7$(n) | CH$_3$ |
| 7. | —NH—COOC$_3$H$_7$(i) | CH$_3$ |
| 8. | —NH—COOC$_4$H$_9$(n) | CH$_3$ |
| 9. | —NH—COOCH$_2$—phenyl | CH$_3$ |
| 10. | CO—NH$_2$ | CO—NH$_2$ |
| 11. | CN | CN |
| 12. | COOH | COOCH$_3$ |
| 13. | COOCH$_3$ | COOCH$_3$ |
| 14. | COOC$_2$H$_5$ | COOC$_2$H$_5$ |
| 15. | CH$_3$ | CO—NH$_2$ |
| 16. | CH$_3$ | COOC$_2$H$_5$ |
| 17. | CH$_3$ | CO—NHNH$_2$ |
| 18. | CH$_3$ | COOH |
| 19. | CN | CO—NH$_2$ |
| 20. | CO—NH—phenyl | CO—NH—phenyl |
| 21. | CH$_3$ | NH—COOC$_2$H$_5$ |
| 22. | CH$_3$ | NH—COOC$_3$H$_7$(n) |
| 23. | CH$_3$ | NH—COOC$_3$H$_7$(i) |
| 24. | CH$_3$ | NH—COOC$_4$H$_9$(n) |
| 25. | CH$_3$ | NH—COOCH$_2$—phenyl |
| 26. | CO—NH—phenyl | CH$_3$ or |
| | CH$_3$ | CO—NH—phenyl | as pharmaceutical active compounds, to their use and to medicaments containing compounds of the formula I.

The above compounds of the formula I are known. They are described, for example, in the publications which follow, in which processes for their preparation are also described:

(a) Ch. Grundmann, G. Nickel, R. K. Bansal, Liebigs Ann. Chem. 1975, 1029;
(b) A. Gasco, V. Mortarini, G. Ruá, E. Menziani, J. Het. Chem. 9, 837, (1972);
(c) A. Gasco, V. Mortarini, G. Ruá, G. M. Nano, E. Menziani ibid 9, 577 (1972);
(d) H. Wieland, E. Gmelin, Liebigs Ann. Chem. 367, 80 (1909);
(e) O. Dimroth, O. Dienstbach, Ber. 41, 4075 (1908)
(f) G. Ponzio, Gazz. chim. ital. 66, 819 (1936).

According to the present state of knowledge, the compound described in the last-mentioned publication, "anilide del perossido dell'acido metilgliossimcarbonico" ("anilide of the peroxide of methylglyoxime-carbonic acid") of melting point 150° to 151° C., has one of the two structures

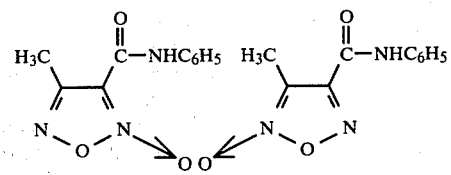

This compound which is mentioned in the above table under No. 26 is prepared by oxidizing β-methylbenzoylglyoxime of the formula

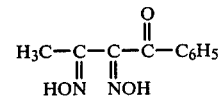

whereby a compound is formed which is named by G. Ponziv loc. cit. as "metilbenzoilperossido", this compound is reacted with hydroxylamine chlorohydrate to form the "β-ossima del metilbenzoilperossido", which is transformed according to a Beckmann rearrangement to the "anilide del perossido dell'acido metilgliossimcarbonico".

It has been found, surprisingly, that the compounds of the formula I possess interesting and therapeutically utilisable pharmacodynamic properties and have a relatively low toxicity. It has been possible to show, in animal experiments, that the compounds of the formula I can be employed in cardiovascular diseases, such as high blood pressure and angina pectoris. The compounds of the formula I and medicaments containing them can also be employed in man for combating or preventing diseases, particularly cardiovascular diseases, such as high blood pressure and angina pectoris.

Amongst the compounds of the formula I, 3-methyl-1,2,5-oxadiazole-2-oxide-4-carboxylic acid amide ($R^1$=CH$_3$ and $R^2$=CONH$_2$), and especially 4-methyl-1,2,5-oxadiazole-2-oxide-3-carboxylic acid amide ($R^1$=CONH$_2$ and $R^2$=CH$_3$) and very particularly 1,2,5-oxadiazole-2-oxide-3,4-dicarboxylic acid diamide ($R^1$=$R^2$=CONH$_2$) are preferred.

The anti-anginous action of the compounds was measured by the following method:

The investigations are carried out on mongrel dogs of both sexes under pentobarbital narcosis (30 to 40 mg/kg administered intravenously), or under urethane-chloralose narcosis (3 ml/kg of urethane/chloralose mixture, administered intravenously=20 mg/kg of chloralose and 250 mg/kg of urethane). The animals were given respiration by means of a Mark 7 Bird respirator. The final expiratory content of carbon dioxide (determined by means of an Uras machine) was between 4.5 and 5% by volume.

During the whole experiment, the animals under pentobarbital narcosis received a continuous intravenous infusion of pentobarbital: 4 mg/kg/6 ml/hour, in order to ensure a constant depth of narcosis; the animals under urethane-chloralose narcosis received no continuous infusion. The infusion was administered through the cephalic vein.

After the experimental animals had been prepared, there was a pause of approx. 1 hour until all the haemodynamic parameters had reached the steady state. The actual experiment was then begun.

The mean blood pressure was measured peripherally in the femoral artery via a Statham pressure recorder.

A Millar tip catheter inserted into the left ventricle via the cardial artery signalled the final diastolic blood pressure relating to the left ventricle and for the heart rate. The mean average blood pressure in the pulmonary artery was measured by means of a second tip catheter inserted via the jugular vein.

The following results were obtained with this method of investigation, for example for 1,2,5-oxadiazole-2-oxide-3,4-dicarboxylic acid diamide (0.1 mg/kg i.d.):

| Parameters | Starting value (mbars) | Change (mbars) | Duration of effect (minutes) |
| --- | --- | --- | --- |
| Pulmonary arterial pressure | 21 | −2.33 | 80 |
| Final diastolic blood pressure relating to the left ventricle | 9 | −3.33 | 80 |
| Mean blood pressure | 136 | −50 | 90 |
| Heart rate (beats/minute) | 101 | +5 | |

At a dosage of 0.1 mg/kg administered intravenously, 4-methyl-1,2,5-oxadiazole-2-oxide-3-carboxylic acid amide exhibited the following effects:

| Parameters | Starting value (mbars) | Change (mbars) | Duration of effect (minutes) |
| --- | --- | --- | --- |
| Pulmonary arterial pressure | 18 | −2.26 | 20 |
| Final diastolic blood pressure relating to the left ventricle | 6.7 | −3.73 | 40 |
| Mean blood pressure | 153 | −33.3 | 60 |
| Heart rate (beats/minute) | 155 | 0 | |

The acute toxicity of 1,2,5-oxadiazole-2-oxide-3,4-dicarboxylic acid diamide was determined on mice, giving an $LD_{50}$ of 167 mg/kg, administered intravenously.

1,2,5-Oxadiazole-2-oxide-3,4-dicarboxylic acid diamide also displayed a pronounced cardiovascular action on rats. The blood pressure was determined on awake, spontaneously hypertonic rats by a surgical method via a catheter implanted into the left carotid artery chronically.

| Dose 10 mg/kg administered orally | Systolic blood pressure (mbars) | Diastolic blood pressure (mbars) |
| --- | --- | --- |
| Starting value | 247 | 206 |
| Change | −56 | −60 |
| Duration of effect | 90 minutes | 90 minutes |

The compounds of the formula I are useful as drugs, for example in the form of pharmaceutical formulations. The pharmaceutical formulations are administered orally, for example in the form of tablets, lacquered tablets, coated tablets, hard and soft gelatin capsules, solutions, syrups, emulsions or suspensions. They are, however, alternatively also administered rectally, for example in the form of suppositories, or parenterally, for example in the form of injection solutions, or percutaneously, for example in the form of ointments.

Tablets, lacquered tablets, coated tablets and hard gelatin capsules are prepared by processing the compounds of the formula I with pharmaceutically inert, inorganic or organic excipients. Examples of excipients which are useful for tablets, coated tablets and hard gelatin capsules are lactose, corn starch or derivatives thereof, talc, stearic acid or salts thereof and the like. Examples of excipients for soft gelatin capsules and suppositories are fats, waxes, semi-solid and liquid polyols, natural or hardened oils and the like. Examples of excipients which are suitable for the preparation of solutions and syrups are water, sucrose, invert sugar, glucose, polyols and the like. Examples of excipients which are suitable for the preparation of injection solutions are water, alcohols, glycerol, polyols, vegetable oils and the like.

In addition, the pharmaceutical formulations optionally contain other substances, such as, for example, disintegrants, preservatives, solubilisers, stabilisers, wetting agents, emulsifiers, sweeteners, colorants, flavourings, salts for varying the osmotic pressure, buffers, coating agents or antioxidants. They optionally contain two or more compounds of the formula I and/or other therapeutically valuable substances.

The compounds of the formula I are used, in accordance with the invention, in combating or preventing diseases of the cardiovascular system, for example as antihypertensive active compounds in the case of the various forms of high blood pressure, in combating or preventing angina pectoris and the like.

The dosage varies within wide limits and is adjusted to the particular data in each individual case.

In general, a daily dose of about 0.1 to 100 mg, preferably 1 to 20 mg, per human individual, of the active substance is appropriate in the case of oral administration. In other forms of application the daily dosis range is similar, i.e. in general also about 0.1 to 100 mg per human individual. The daily dose is normally administered in several partial, for example 2 to 4 doses, the single dose containing 0.001 to 1 mg per kg of body weight of the active substance. The concentration of the active substance of the preparations is 0.01 to 20%, preferably 0.05 to 10% per single dosis, relative to the total weight of the preparation.

In the examples which follow and which illustrate the present invention but are not intended to limit its scope in any way, pharmaceutical formulations which contain 1,2,5-oxadiazole-2-oxide-3,4-dicarboxylic acid diamide are described as the active compound.

EXAMPLE 1

Soft gelatin capsules, containing 5 mg of active compound per capsule:

| | per capsule |
| --- | --- |
| Active compound | 5 mg |
| Mixture of triglycerides obtained by fractionation from coconut oil | 150 mg |
| Contents of capsule | 155 mg |

EXAMPLE 2

Injection solution, containing 1 mg of active compound per ml:

| | per ml |
| --- | --- |
| Active compound | 1.0 mg |
| Polyethylene glycol 400 | 0.3 ml |
| Sodium chloride | 2.7 mg |

-continued

| | per ml |
|---|---|
| Water for injection purposes | ad 1 ml |

EXAMPLE 3

Emulsions, containing 3 mg of active compound per 5 ml

| | per 100 ml of emulsion |
|---|---|
| Active compound | 0.06 g |
| Neutral oil | q.s. |
| Sodium carboxymethylcellulose | 0.6 g |
| Polyoxyethylene stearate | q.s. |
| Pure glycerol | 0.2 to 2.0 g |
| Flavouring substance | q.s. |
| Water (demineralised or distilled) | ad 100 ml |

EXAMPLE 4

Rectal formulation, containing 4 mg of active compound per suppository

| | per suppository |
|---|---|
| Active compound | 4 mg |
| Suppository base composition | ad 2 g |

EXAMPLE 5

Tablets, containing 2 mg of active compound per tablet

| | per tablet |
|---|---|
| Active compound (finely ground) | 2 mg |
| Corn starch (white) | 150 mg |
| Lactose | 60 mg |
| Microcrystalline cellulose | 50 mg |
| Polyvinylpyrrolidone | 20 mg |
| Magnesium stearate | 2 mg |
| Sodium carboxymethyl-starch | 25 mg |
| | 309 mg |

The invention and its advantages are readily understood from the preceding description. Various changes may be made in the dosage forms, the medicament compositions, the mode of administering without departing from the spirit and scope of the invention or sacrificing its material advantages. The hereinbefore described aspects of the subject invention are merely illustrative of preferred embodiments.

What is claimed is:

1. A pharmaceutical composition useful for treating or preventing human cardiovascular-system disease and comprising a pharmacologically-active component and physiologically-acceptable pharmacologically-inert excipient, the pharmacologically-active component comprising from 0.01 to 20 percent by weight, based on the total composition weight, of a 1,2,5-oxadiazole-2-oxide having the structure of (a) the 3-methyl ester of 1,2,5-oxadiazole-2-oxide-3,4-dicarboxylic acid, (b) 3-methyl-1,2,5-oxadiazole-2-oxide-4-carboxylic acid-anilide or (c) 4-methyl-1,2,5-oxadiazole-2-oxide-3-carboxylic acid-anilide.

2. A pharmaceutical composition according to claim 1 comprising, per unit dose, from 0.1 to 100 milligrams of the 3-methylester of 1,2,5-oxadiazole-2-oxide-3,4-dicarboxylic acid.

3. A pharmaceutical composition according to claim 1 wherein the 1,2,5-oxadiazole has the structure of 3-methyl-1,2,5-oxadiazole-2-oxide-4-carboxylic acid-anilide.

4. A pharmaceutical composition according to claim 1 wherein the 1,2,5-oxadiazole has the structure of 4-methyl-1,2,5-oxadiazole-2-oxide-3-carboxylic acid-anilide.

5. A method of treating or preventing cardiovascular system disease which comprises administering to a human, subject to or afflicted with such disease, an effective amount of a pharmaceutical composition comprising a pharmacologically-active component and physiologically-acceptable pharmacologically-inert excipient, the pharmacologically-active component comprising from 0.01 to 20 percent by weight, based on the total composition weight, of 1,2,5-oxadiazole-2-oxide of formula I

wherein $R^1$ and $R^2$ have the following meaning:

| | $R^1$ | $R^2$ |
|---|---|---|
| 1. | CO—NH$_2$ | CH$_3$ |
| 2. | COOC$_2$H$_5$ | CH$_3$ |
| 3. | CO—NHNH$_2$ | CH$_3$ |
| 4. | COOH | CH$_3$ |
| 5. | —NH—COOC$_2$H$_5$ | CH$_3$ |
| 6. | —NH—COOC$_3$H$_7$(n) | CH$_3$ |
| 7. | —NH—COOC$_3$H$_7$(i) | CH$_3$ |
| 8. | —NH—COOC$_4$H$_9$(n) | CH$_3$ |
| 9. | —NH—COOCH$_2$—phenyl | CH$_3$ |
| 10. | CO—NH$_2$ | CO—NH$_2$ |
| 11. | CN | CN |
| 12. | COOH | COOCH$_3$ |
| 13. | COOCH$_3$ | COOCH$_3$ |
| 14. | COOC$_2$H$_5$ | COOC$_2$H$_5$ |
| 15. | CH$_3$ | CO—NH$_2$ |
| 16. | CH$_3$ | COOC$_2$H$_5$ |
| 17. | CH$_3$ | CO—NHNH$_2$ |
| 18. | CH$_3$ | COOH |
| 19. | CN | CO—NH$_2$ |
| 20. | CO—NH—phenyl | CO—NH—phenyl |
| 21. | CH$_3$ | NH—COOC$_2$H$_5$ |
| 22. | CH$_3$ | NH—COOC$_3$H$_7$(n) |
| 23. | CH$_3$ | NH—COOC$_3$H$_7$(i) |
| 24. | CH$_3$ | NH—COOC$_4$H$_9$(n) |
| 25. | CH$_3$ | NH—COOCH$_2$—phenyl |
| 26. | CO—NH—phenyl CH$_3$ | CH$_3$ or CO—NH—phenyl |

6. A method of treating or preventing high blood pressure or angina pectoris which comprises administering to a human, subject to or afflicted with one or both of such conditions, an effective amount of a pharmaceutical composition comprising a pharmacologically-active component and physiologically-acceptable pharmacologically-inert excipient, the pharmacologically-active component comprising from 0.01 to 20 percent by weight, based on the total composition weight, of (a) 3-methyl-1,2,5-oxadiazole-2-oxide-4-carboxylic acid amide, (b) 4-methyl-1,2,5-oxadiazole-2-oxide-3-carboxylic acid amide or (c) 1,2,5-oxadiazole-2-oxide-3,4-dicarboxylic acid diamide.

7. A method according to claim 6 wherein the pharmaceutical composition has an effective amount per unit dose of (a).

8. A method according to claim 6 wherein the pharmaceutical composition has an effective amount per unit dose of (b).

9. A method according to claim 6 wherein the pharmaceutical composition has an effective amount per unit dose of (c).

* * * * *